United States Patent
Quinones

[11] Patent Number: 6,029,900
[45] Date of Patent: Feb. 29, 2000

[54] AIR FRESHENER DEVICE

[76] Inventor: Jorge A. Quinones, 15 Jordan Dr., C-3, Whitehall, Pa. 18052

[21] Appl. No.: 09/143,807

[22] Filed: Aug. 31, 1998

[51] Int. Cl.[7] ........................................ A61L 9/12
[52] U.S. Cl. .............................. 239/47; 239/51.5; 239/57; 239/58
[58] Field of Search .............................. 239/47, 49, 51.5, 239/57, 58, 59, 60

[56] References Cited

U.S. PATENT DOCUMENTS

| | | | |
|---|---|---|---|
| 472,133 | 4/1892 | Merrill | 239/51.5 |
| 2,086,631 | 7/1937 | Munro | 239/59 X |
| 2,092,728 | 9/1937 | Dearling | 239/51.5 |
| 2,529,536 | 11/1950 | Bjorksten | 239/51.5 |
| 3,565,339 | 2/1971 | Curran | 239/60 |
| 3,706,140 | 12/1972 | Brillaud et al. | 34/60 |
| 3,727,840 | 4/1973 | Nigro | 239/47 X |
| 4,995,555 | 2/1991 | Woodruff | 239/43 |
| 5,000,383 | 3/1991 | Van Der Heijden | 239/47 |
| 5,299,736 | 4/1994 | Greene | 239/56 |
| 5,544,812 | 8/1996 | Torres | 239/55 |

*Primary Examiner*—Robert M. Fetsuga
*Attorney, Agent, or Firm*—Henderson & Sturm LLP

[57] ABSTRACT

A bomb shaped air freshener device 10 including a hollow spherical housing member 20 dimensioned to receive a scent dispensing unit 12. The upper portion 21 of the housing member 20 is provided with at least one scent dispensing aperture 25 and operatively associated with an adjustable closure unit 13 wherein at least a portion 65 of the adjustable closure unit 13 is dimensioned and configured to resemble the fuse of a bomb.

15 Claims, 2 Drawing Sheets

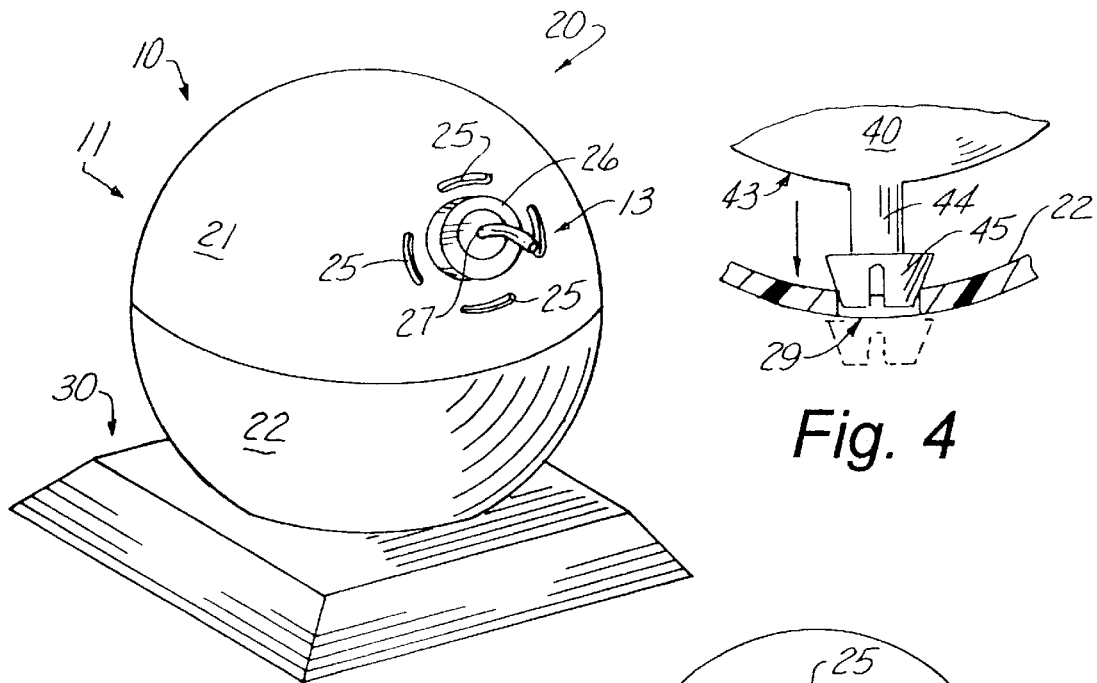
Fig. 4
Fig. 1
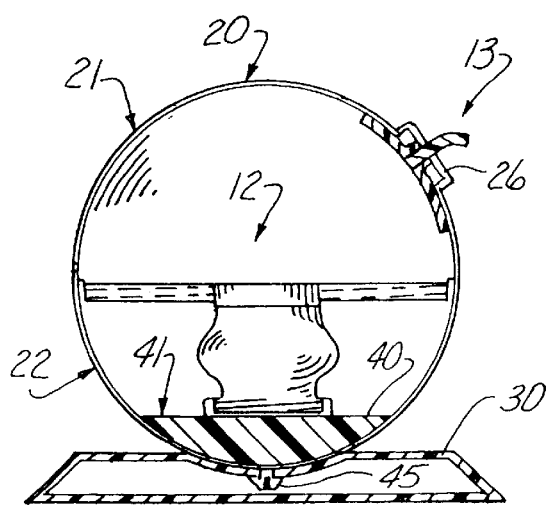
Fig. 2
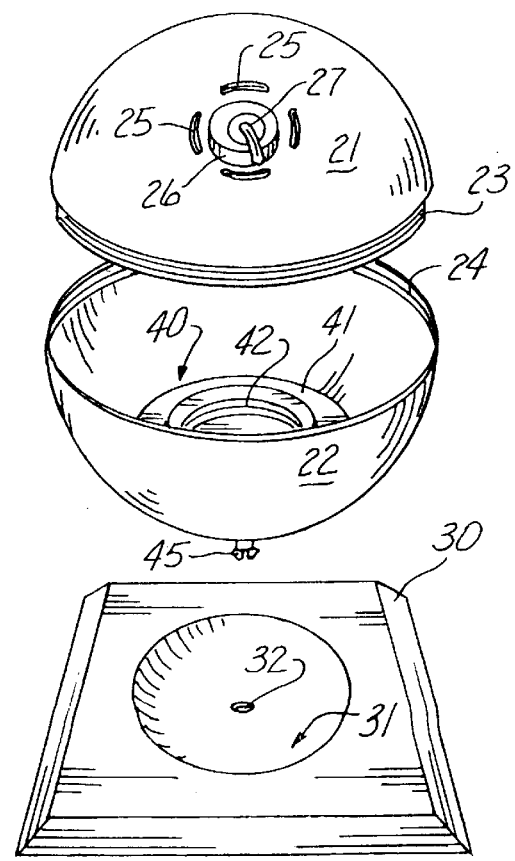
Fig. 3

AIR FRESHENER DEVICE

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of air freshener devices in general, and in particular to a bomb shaped air freshener device wherein the simulated fuse portion of the bomb shaped device is part of an adjustable closure mechanism.

2. Description of Related Art

As can be seen by reference to the following U.S. Pat. Nos. 3,706,140; 4,995,555; 5,299,736; and 5,544,812, the prior art is replete with myriad and diverse air freshener devices having both functional and aesthetically pleasing features.

While all of the aforementioned prior art constructions are more than adequate for the basic purpose and function for which they have been specifically designed, they are uniformly deficient with respect to their failure to provide a simple, efficient, and practical air freshener which not only has an aesthetically pleasing and humorous external appearance, but also utilizes one of the major components of the external configuration as a control lever to adjust the amount of air freshener that is dispensed from the device.

As most marketing professionals are aware, when you are able to marry a functional device with an aesthetically pleasing appearance, the volume of sales of the particular item will be proportionately larger than the same type of item that is functionally identical, but which does not possess the same visual impact.

As a consequence of the foregoing situation, there has existed a longstanding need for a new and improved style of air freshener that combines form and function in an aesthetically pleasing and humorous fashion, and the provision of such a construction is a stated objective of the present invention.

BRIEF SUMMARY OF THE INVENTION

Briefly stated, the air freshener device that forms the basis of the present invention comprises a generally bomb shaped housing unit which contains a scent dispensing unit and is further provided with an adjustable closure unit which at least in part resembles the fuse of the simulated bomb.

As will be explained in greater detail further on in the specification, the housing unit comprises a hollow spherical housing member having an upper portion and a lower portion wherein the lower housing portion is dimensioned to receive the scent dispensing unit and the upper portion is provided with a plurality of scent dispensing apertures that are selectively covered by the adjustable closure unit.

In addition, the adjustable closure unit includes a closure member having a plurality of closure elements disposed on the interior of the upper housing portion and an actuating lever that extends through the upper housing portion and resembles a bomb fuse. The rotation of the simulated bomb fuse selectively uncovers the plurality of scent dispensing apertures.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a perspective view of the air freshener device that forms the basis of the present invention;

FIG. 2 is a cross sectional view of the device;

FIG. 3 is an exploded perspective view of the housing unit;

FIG. 4 is an isolated detail view of the engagement between the housing unit and the scent dispensing unit;

DETAILED DESCRIPTION OF THE INVENTION

Figure 5:
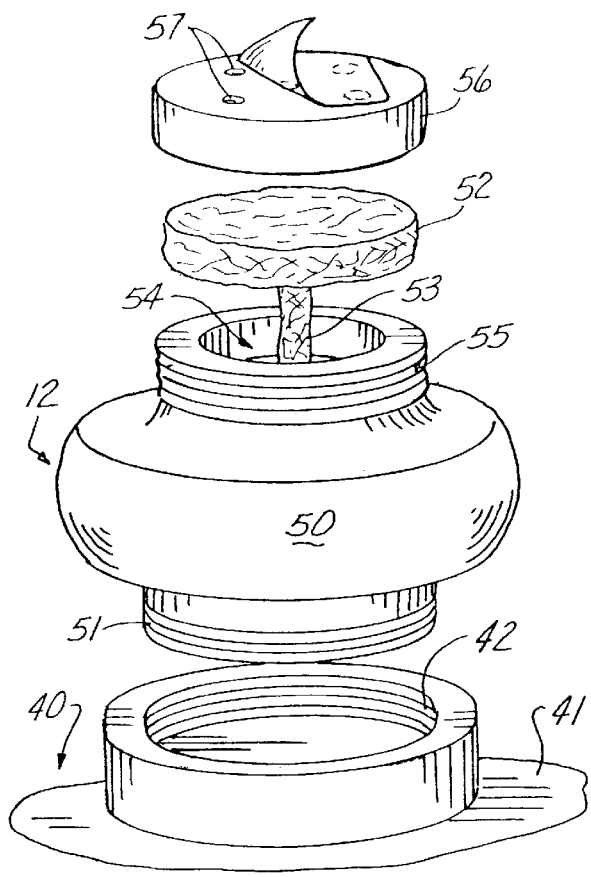
FIG. 5 is an exploded perspective view of the scent dispensing unit.

As can be seen by reference to the drawings, and in particularly to FIG. 1, the air freshener device that forms the basis of the present invention is designated generally by the reference number 10. The device 10 comprises in general, a housing unit 11, a scent dispensing unit 12, and an adjustable closure unit 13. These units will now be described in seriatim fashion.

As shown in FIGS. 1 through 4, the housing unit 11 comprises in general a generally spherical housing member 20 having hemispherical upper 21 and lower 22 portions provided with complementary threads 23 and threaded recesses 24 for joining the hemispherical upper 21 and lower 22 portions together in a well recognized fashion.

In addition, the upper portion 21 of the housing member 20 is provided with a plurality of air slots 25 which surround a short cylindrical projection 26 provided with a discrete opening 27 and the lower portion 22 of the housing member 20 is provided with a short discrete central aperture 29 whose purpose and function will be described presently.

Still referring to FIGS. 1 through 4, it can be seen that the housing unit 11 also comprises an enlarged generally rectangular base member 30 having an enlarged central recess 31 formed therein to receive the bottom of the lower housing portion 22. The central recess 31 is further provided with a central aperture 32 which is alignable with the central aperture 29 in the lower housing portion 22.

Turning now to FIGS. 2 through 5, it can be seen that the housing unit 11 also includes a connector element 40 for operatively engaging the housing member 20 with the base member 30. The connector element 40 having a generally flat upper surface 41 provided with a threaded recess 42 and having a generally arcuate lower surface 43 dimensioned to conform to the interior of the lower portion 22 and provided with a downwardly depending post element 44 having a resiliently deformable head 45 dimensioned to pass through the central aperture 29 in the lower housing portion 22 and to be releasably engaged in the central aperture 32 in the enlarged recess 31 of the base member 30 to connect the housing member 20 to the base member 30 in a well recognized fashion.

As can also be seen by reference to FIGS. 2 and 5, the scent dispensing unit 12 comprises a hollow receptacle member 50 having a threaded lower portion 51 dimensioned to be threadedly received in the threaded recess 42 of the connector element 40 to maintain the receptacle member 50 in a vertically upright position.

In addition, the scent dispensing unit 12 further comprises an absorbent wick member 52 having a wick stem 53 dimensioned to be received within the open mouth 54 of the receptacle member 50. The receptacle member 50 may further be provided with a threaded neck portion 55 to receive an optional cap element 56 provided with a plurality of apertures 57 to limit the evaporation rate of the air freshening medium (not shown) contained within the interior of the receptacle member 50 wherein the air freshening medium can be in liquid, rote, or gel form and in the latter two instances would not require the presence of the wick member 52.

Figure 7:
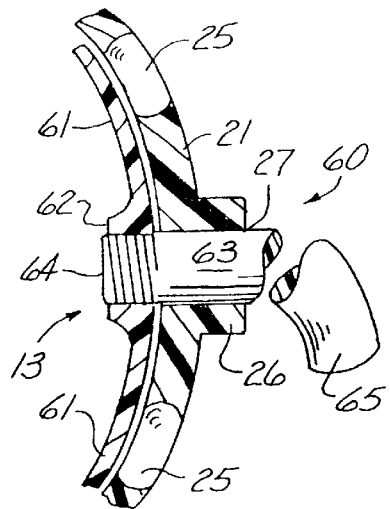
FIG. 7 is an isolated cross sectional view of the adjustable closure unit and the upper portion of the housing member.
Figure 8:
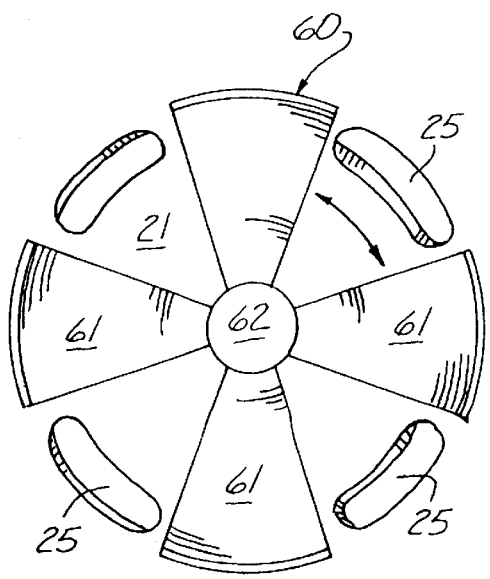
FIG. 8 is a view of the adjustable closure unit as seen from inside the upper portion of the housing member.

Turning now to FIGS. 7 and 8, it can be seen that the adjustable closure unit 13 comprises a generally fan shaped closure member 60 having a plurality of fan blade shaped closure elements 61 projecting radially outwardly from a central hub element 62. Each of the closure elements 61 are dimensioned to overlie one of the plurality of apertures 25 formed in the upper housing portion 21.

In addition, the closure member 60 is further provided with an actuating lever 63 dimensioned to be received through the discrete aperture 27 in the short cylindrical projection 26 which extends outwardly from the upper housing portion 21 of the housing member 20 wherein the inboard end 64 of the lever 63 is threadedly engaged in the hub element 62 and the outboard end 65 of the lever 63 is curved and configured to resemble the fuse of a bomb.

Figure 6:
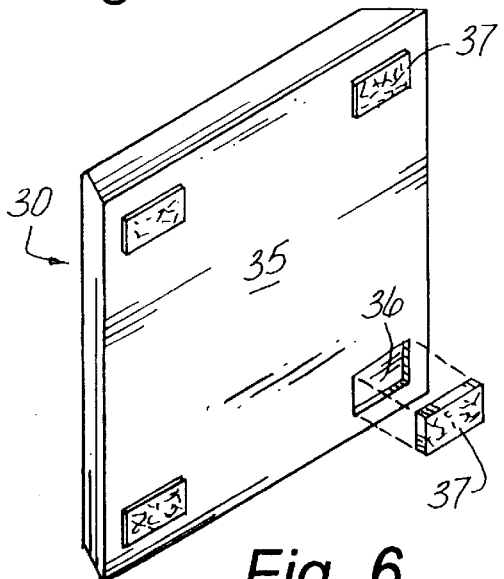
FIG. 6 is an isolated detail view of the bottom of the base member.

As shown in FIG. 6, the bottom surface 35 of the base member 30 is provided with a plurality of recesses 36 dimensioned to receive foot pad elements 37 that are provided with a high friction or adhesive surface for maintaining the device 10 on a non stable surface such as a vehicle dashboard or the like.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

What is claimed is:

1. A bomb shaped air freshener device comprising:
   a generally hollow spherical housing member including an upper portion and a lower portion wherein the upper housing portion is provided with at least one scent dispensing aperture;
   a scent dispensing unit dimensioned to be received within the interior of the hollow spherical housing member and including a hollow receptacle member dimensioned to receive a quantity of air freshening medium;
   an adjustable closure unit operatively associated with the upper portion of the housing member to selectively uncover a portion of said at least one scent dispensing aperture wherein a portion of the closure unit is configured to resemble the fuse of a bomb; and
   a base member provided with an enlarged recess to receive the bottom of the lower housing portion wherein the base member has a bottom surface provided with means for engaging the base member with an unstable surface.

2. The device as in claim 1 wherein the scent dispensing unit is disposed within the lower housing portion.

3. The device as in claim 2 wherein the scent dispensing unit is further disposed within the recess in the base member.

4. The device as in claim 1 wherein the upper portion of the housing member is provided with a short cylindrical projection and a portion of the adjustable closure unit is dimensioned to be rotatably received in said short cylindrical projection.

5. The device as in claim 4 wherein the upper housing portion is provided with a plurality of scent dispensing apertures which surround said short cylindrical projection.

6. The device as in claim 5 wherein the adjustable closure unit comprises:
   a plurality of closure elements configured to overlie said plurality of scent dispensing apertures wherein said plurality of closure elements are connected to a central hub element; and, an actuating lever operatively engaged on one end to said central hub.

7. The device as in claim 6 wherein said actuating lever is operatively associated with said short cylindrical projection on the upper housing portion.

8. The device as in claim 7 wherein said actuating lever projects through said short cylindrical projection.

9. The device as in claim 8 wherein the actuating lever has an inboard end connected to said central hub and an outboard end dimensioned and configured to represent the fuse of a bomb.

10. A bomb shaped air freshener device comprising:
    a generally hollow spherical housing member including an upper portion and a lower portion wherein the upper housing portion is provided with at least one scent dispensing aperture;
    a scent dispensing unit dimensioned to be received within the interior of the hollow spherical housing member and including a hollow receptacle member dimensioned to receive a quantity of air freshening medium; and
    an adjustable closure unit operatively associated with the upper portion of the housing member to selectively uncover a portion of said at least one scent dispensing aperture wherein a portion of the closure unit is configured to resemble the fuse of a bomb wherein the upper portion of the housing member is provided with a short cylindrical projection and a portion of the adjustable closure unit is dimensioned to be rotatably received in said short cylindrical projection.

11. The device as in claim 10 wherein the upper housing portion is provided with a plurality of scent dispensing apertures which surround said short cylindrical projection.

12. The device as in claim 11 wherein the adjustable closure unit comprises:

a plurality of closure elements configured to overlie said plurality of scent dispensing apertures wherein said plurality of closure elements are connected to a central hub element; and, an actuating lever operatively engaged on one end to said central hub.

13. The device as in claim 12 wherein said actuating lever is operatively associated with said short cylindrical projection on the upper housing portion.

14. The device as in claim 13 wherein said actuating lever projects through said short cylindrical projection.

15. The device as in claim 14 wherein the actuating lever has an inboard end connected to said central hub and an outboard end dimensioned and configured to represent the fuse of a bomb.

* * * * *